United States Patent [19]
Berman

[11] Patent Number: 5,985,679
[45] Date of Patent: *Nov. 16, 1999

[54] AUTOMATED ENDPOINT DETECTION SYSTEM DURING CHEMICAL-MECHANICAL POLISHING

[75] Inventor: Michael J. Berman, West Linn, Oreg.

[73] Assignee: LSI Logic Corporation, Milpitas, Calif.

[*] Notice: This patent is subject to a terminal disclaimer.

[21] Appl. No.: 08/874,055

[22] Filed: Jun. 12, 1997

[51] Int. Cl.$^6$ ............................. B24B 49/00; B24B 14/12
[52] U.S. Cl. .................................. 438/7; 438/8; 438/14; 438/692; 156/345
[58] Field of Search ............................ 438/7, 8, 14, 692; 156/345

[56] References Cited

U.S. PATENT DOCUMENTS

| | | |
|---|---|---|
| 4,772,127 | 9/1988 | Chase et al. . |
| 4,794,264 | 12/1988 | Quackenbos et al. . |
| 4,898,471 | 2/1990 | Stonestrom et al. . |
| 4,943,734 | 7/1990 | Johnson et al. . |
| 5,032,217 | 7/1991 | Tanaka ..................................... 156/640 |
| 5,049,816 | 9/1991 | Moslehl ................................... 324/158 |
| 5,058,982 | 10/1991 | Katzir . |
| 5,076,692 | 12/1991 | Neukermans et al. . |
| 5,153,668 | 10/1992 | Katzir et al. . |
| 5,308,438 | 5/1994 | Cote et al. .............................. 156/636 |
| 5,355,212 | 10/1994 | Wells et al. . |
| 5,389,794 | 2/1995 | Allen et al. . |
| 5,413,941 | 5/1995 | Koos et al. ................................ 438/16 |
| 5,433,651 | 7/1995 | Lustig et al. .............................. 451/16 |
| 5,563,702 | 10/1996 | Emery et al. . |
| 5,572,598 | 11/1996 | Wihl et al. . |
| 5,618,461 | 4/1997 | Burke et al. ............................. 219/502 |
| 5,708,506 | 1/1998 | Birang ..................................... 438/692 |
| 5,783,804 | 7/1998 | Burke et al. ............................. 219/494 |
| 5,835,225 | 11/1998 | Thakur .................................... 356/381 |

OTHER PUBLICATIONS

U.S. application No. 08/869,278, Berman, filed Jun. 4, 1997.

*Primary Examiner*—Benjamin Utech
*Assistant Examiner*—Lynette T. Umez-Eronini
*Attorney, Agent, or Firm*—Beyer & Weaver, LLP

[57] ABSTRACT

An automated endpoint detection process includes obtaining a baseline graph of reflected radiation signal versus time of radiation exposure for a standard integrated circuit substrate surface that is substantially free of residual metal, directing radiation generated from a radiation source through a radiation transparent region of a polishing pad such that radiation is incident on at least a portion of a surface of the integrated circuit substrate, detecting a reflected radiation signal from the integrated circuit substrate surface through the radiation transparent region of the polishing pad, comparing an area under a graph of the reflected radiation signal versus time of radiation exposure obtained for the integrated circuit surface to the baseline graph of the standard integrated circuit substrate surface and thereby determining whether residual metal is present on the surface of the integrated circuit substrate and signaling the chemical-mechanical polishing assembly to stop polishing after polishing for a predetermined time, if the area under the graph of the reflected radiation signal versus time of radiation exposure obtained for the integrated circuit surface is substantially equal to the baseline graph of the standard integrated circuit substrate surface.

12 Claims, 5 Drawing Sheets

AUTOMATED ENDPOINT DETECTION SYSTEM DURING CHEMICAL-MECHANICAL POLISHING

CROSS REFERENCE TO RELATED APPLICATIONS

This patent application is related to U.S. patent application Ser. No. 08/869,278 filed on Jun. 4, 1997, pending, naming M. Berman as inventor, and titled "AN AUTOMATED INSPECTION SYSTEM FOR RESIDUAL METAL AFTER CHEMICAL MECHANICAL POLISHING".

BACKGROUND OF THE INVENTION

The present invention relates to automated endpoint detection systems during chemical-mechanical polishing (commonly known in the art as "CMP") of an integrated circuit substrate. More particularly, the present invention relates to automated endpoint detection systems that employ radiation sources and detectors to direct and detect radiation through a polishing pad to test for residual metal on an integrated circuit substrate during CMP.

CMP typically involves mounting a semiconductor wafer face down on a holder, and rotating the wafer against a polishing pad mounted on a platen, which in turn is rotating or is in an orbital state. A slurry containing a chemical that chemically interacts with the facing wafer layer and an abrasive that physically removes that layer is flowed between the wafer and the polishing pad or on the pad near the wafer. This technique is commonly applied to planarize metallization layers in the semiconductor wafer.

An endpoint determination mechanism currently employed during CMP to determine a polishing endpoint of a wafer layer includes a motor current measuring mechanism, as disclosed in U.S. Pat. No. 5,308,438, which is incorporated herein by reference in its entirety for all purposes. Briefly, according to this patent, the endpoint determination mechanism includes a motor, which rotates the wafer against a polishing pad. The power required to maintain a set rotational speed in the rotating motor changes (sometimes significantly) when a layer is removed from the wafer surface and a new wafer layer is being polished. In other words, as a layer is removed from the wafer surface, the amount of current being drawn by the motor changes due to the change in the frictional force induced by the changing wafer surface. Thus, by measuring the change in the current being drawn by the motor during polishing, the CMP endpoint of a wafer layer may be determined.

Endpoint determination using the motor current measuring mechanism, however, provides an average signal and is therefore imprecise, i.e. the motor current is not sensitive to the full surface of the wafer area during the monitoring of the polishing process. FIG. 1 shows the surface of a semiconductor wafer 100 that may result when the endpoint for CMP is determined by employing a motor current. As shown in FIG. 1, a plurality of die (or integrated circuits) 102 are formed on the surface of wafer 100, which has residual metal regions 104 that are large enough, i.e. on the order of several square millimeters, to cover several of die 102. Residual metal regions 104 represent underpolished or not completely polished metallization regions of the wafer surface that may render one or more die inoperable.

What is therefore needed is an improved endpoint detection system for detecting residual metal on an integrated circuit substrate that more precisely determines the CMP endpoint than the conventional polishing techniques.

SUMMARY OF THE INVENTION

To achieve the foregoing, the present invention provides an automated endpoint detection process for detecting residual metal on a surface of an integrated circuit substrate during chemical-mechanical polishing. The endpoint detection process includes obtaining a baseline graph of reflected radiation signal versus time of radiation exposure for a standard integrated circuit substrate surface that is substantially free of residual metal, directing radiation generated from a radiation source through a radiation transparent region of a polishing pad such that radiation is incident on at least a portion of a surface of the integrated circuit substrate, detecting a reflected radiation signal from the integrated circuit substrate surface through the radiation transparent region of the polishing pad, comparing an area under a graph of the reflected radiation signal versus time of radiation exposure obtained for the integrated circuit surface to the baseline graph of the standard integrated circuit substrate surface and thereby determining whether residual metal is present on the surface of the integrated circuit substrate and signaling the chemical-mechanical polishing assembly to stop polishing after polishing for a predetermined time, if the area under the graph of the reflected radiation signal versus time of radiation exposure obtained for the integrated circuit surface is substantially equal to the baseline graph of the standard integrated circuit substrate surface.

In one embodiment of the present invention, the step of obtaining the baseline graph of the reflected radiation signal versus time of radiation exposure for the surface on the standard integrated circuit substrate is conducted before the step of polishing. The step of comparing the area under the graph of the reflected radiation signal versus time of radiation exposure obtained for the integrated circuit to the baseline graph of the standard integrated circuit substrate and the step of signaling as described above may be facilitated by a computer system. In the step of signaling, the predetermined time may be between about 2 and about 5 seconds.

The step of obtaining the baseline graph as mentioned above may include providing radiation to the surface of the standard integrated circuit substrate that is substantially free of residual metal through the radiation transparent region of the polishing pad, which is rotating or in an orbital state, such that radiation is incident on at least a portion of the surface of the standard integrated circuit substrate. The step of obtaining the baseline graph further includes detecting the baseline reflected radiation signal from the surface of the standard integrated circuit substrate through the radiation transparent region of the polishing pad over a period of time, during which substantially all of the surface of the standard integrated circuit substrate is scanned by radiation and storing the baseline graph of reflected radiation signal versus time of radiation exposure from the surface of the integrated circuit substrate on machine readable media.

The radiation source employed in the endpoint detection process may include an infrared radiation source and the step of detecting may include using a radiation detector that includes an infrared radiation detector. The integrated circuit substrate may include a semiconductor wafer. During the step of directing as mentioned above, substantially all of the integrated circuit surface is exposed to radiation through the radiation transparent region in the polishing pad, which is rotating or in an orbital state. The polishing pad employed in the endpoint detection process of the present invention may include at least one material selected from the group consisting of urethane, polyurethane, felt, polymer and a filler material. The radiation transparent region comprises at least one material selected from the group consisting of silicon dioxide, magnesium oxide, polymetric material, urethane and polyurethane.

In another aspect, the present invention provides a polishing pad for polishing an integrated circuit. The polishing pad includes a material substantially impermeable to radiation and a radiation transparent region in the material and capable of allowing incident and reflected radiation to pass therethrough.

The material in the polishing pad may include at least one material selected from the group consisting of urethane, polyurethane, felt, polymer and a filler material. The radiation transparent region may includes at least one material selected from the group consisting of silicon dioxide, magnesium oxide, polymetric material, urethane and polyurethane. The radiation transparent region in the polishing pad may include a slit. The slit may have a length that ranges from slightly larger than half a diameter of the integrated circuit substrate to slightly larger than the diameter of the integrated circuit substrate. The slit may have a length that is between about 75 and about 450 mm.

In yet another aspect, the present invention provides an apparatus for detecting residual metal on an integrated circuit substrate during chemical-mechanical polishing. The apparatus includes a polishing pad for polishing a surface of an integrated circuit. The polishing pad further includes a material substantially impermeable to radiation and a radiation transparent region in the material, which region is capable of allowing incident and reflected radiation to pass therethrough. The apparatus further includes a radiation source for generating radiation on at least a portion of a surface of the integrated circuit substrate through the radiation transparent region in a polishing pad, a radiation detector for detecting a reflected radiation signal from the substrate surface, and a housing, inside which the radiation source and the detector are positioned appropriately such that radiation directed by the radiation source passes through the radiation transparent region in polishing pad and is incident on the surface of the integrated circuit substrate resulting in a reflected radiation signal from the surface of the integrated circuit substrate that passes through the radiation transparent region and is detected by the detector.

The apparatus of detecting residual metal during integrated circuit substrate chemical-mechanical polishing may further include a band pass filter positioned between the radiation transparent region and the detector such that a reflected radiation signal passes through the band pass filter before reaching the detector. The apparatus may further still include deflectors appropriately positioned at the sides of the radiation source to facilitate a substantial amount of radiation generated from the radiation source to pass through the radiation transparent region.

The polishing pad may include one material selected from the group consisting of urethane, polyurethane, felt, polymer and a filler material. The radiation transparent material may include at least one material selected from the group consisting of silicon dioxide, magnesium oxide, polymetric material, urethane and polyurethane. The radiation transparent region may include a radiation transparent slit. A length of the slit may be between slightly larger than half a diameter of the surface of the integrated circuit and slightly larger than the diameter of the surface of the integrated circuit. A width of the slit may be between about 2 and about 9 mm. The radiation source may include an infrared radiation lamp or halogen lamp. The radiation detector may include a detector capable of detecting infrared radiation.

In yet another aspect, the present invention provides an apparatus for detecting residual metal on an integrated circuit substrate during chemical-mechanical polishing. The apparatus includes a means for polishing a surface of an integrated circuit. The means for polishing further includes a material substantially impermeable to radiation and means for allowing radiation to pass therethrough in the material. The apparatus further includes means for generating radiation on at least a portion of a surface of the integrated circuit substrate through the means for allowing radiation to pass therethrough in the means for polishing. The apparatus further still includes means for detecting a reflected radiation signal from the substrate surface and a housing, inside which the means for generating and the means for detecting are positioned appropriately such that radiation generated by the means for generating passes through the means for allowing radiation to pass therethrough in means for polishing and is incident on the surface of the integrated circuit substrate resulting in a reflected radiation signal from the surface of the integrated circuit substrate that passes through the means for allowing radiation to pass therethrough and is detected by the means for detecting.

The apparatus may further include means for filtering positioned between the means for allowing radiation to pass therethrough and the means for detecting such that a reflected radiation signal passes through the means for filtering before reaching the means for detecting. The apparatus may further still include means for deflecting appropriately positioned at the sides of the means for generating to facilitate a substantial amount of radiation generated from the means for generating to pass through the means for allowing radiation to pass therethrough.

The endpoint detection processes of the present invention represents a marked improvement over the current endpoint detection processes. By way of example, the endpoint detection system of the present invention provides a more precise endpoint during CMP because it may be configured to scan the entire surface and thereby eliminate substantially all the residual metal regions. Thus, the presence of residual metal regions on the substrate surface, as shown in FIG. 1 and encountered when detecting the endpoint by the conventional motor current method are substantially eliminated. This translates into a higher yield for the die. As a further example, the present invention essentially requires a radiation source, a detector, and a polishing pad with a radiation transparent region, all of which are relatively inexpensive and easy to implement. Such equipment can be easily integrated into the CMP apparatus, e.g. CMP apparatus 200 as shown in FIG. 2A, with minor modifications. Further still, the endpoint detection system may also provide immediate feedback to the CMP apparatus under operation to correct CMP parameters for effective polishing.

These and other features of the present invention will be described in more detail below in the detailed description of the invention and in conjunction with the following figures.

DETAILED DESCRIPTION OF THE PREFERRED EMBODIMENTS

The present invention provides an automated endpoint detection system for chemical-mechanical polishing (CMP) that employs radiation sources and detectors that direct and detect radiation through a polishing pad to test for residual metal on an integrated circuit (IC) undergoing chemical-mechanical polishing (CMP). In the following description, numerous specific details are set forth in order to fully illustrate a preferred embodiment of the present invention. It will be apparent, however, that the present invention may be practiced without limitation to some specific details presented herein.

While intending not to be bound by theory, the present invention recognizes that metals and silicon reflect radiation differently. Infrared radiation, for example, passes through a silicon layer, but reflects off a metal layer. The present invention, therefore, employs a polishing pad with a radiation transparent region, through which radiation generated from a radiation source is incident upon a substrate surface that is undergoing CMP. Almost instantly, i.e. within a few milliseconds, a resulting reflected radiation signal off the substrate surface travels through the radiation transparent region and is detected by a radiation detector. A reflected radiation signal is, therefore, obtained over a period of time, during which the entire substrate surface is scanned by radiation passing through a radiation transparent region in a polishing pad.

In this manner, a baseline graph of reflected radiation signal versus time is obtained for a standard IC substrate that is substantially free of residual metal and a graph of reflected radiation signal versus time is obtained for a production IC substrate. The area under the graph of reflected radiation signal versus time of the production IC substrate surface is then monitored during CMP and compared to the area under the baseline graph of the standard IC substrate surface. If the area under this graph of the production IC substrate surface substantially equals the area under the baseline graph of the standard IC substrate surface, then a signal is sent to the CMP apparatus to stop polishing after a predetermined period of time. The present invention represents a marked improvement over the current endpoint detection mechanism and such advantages are set forth below.

Figure 2A:
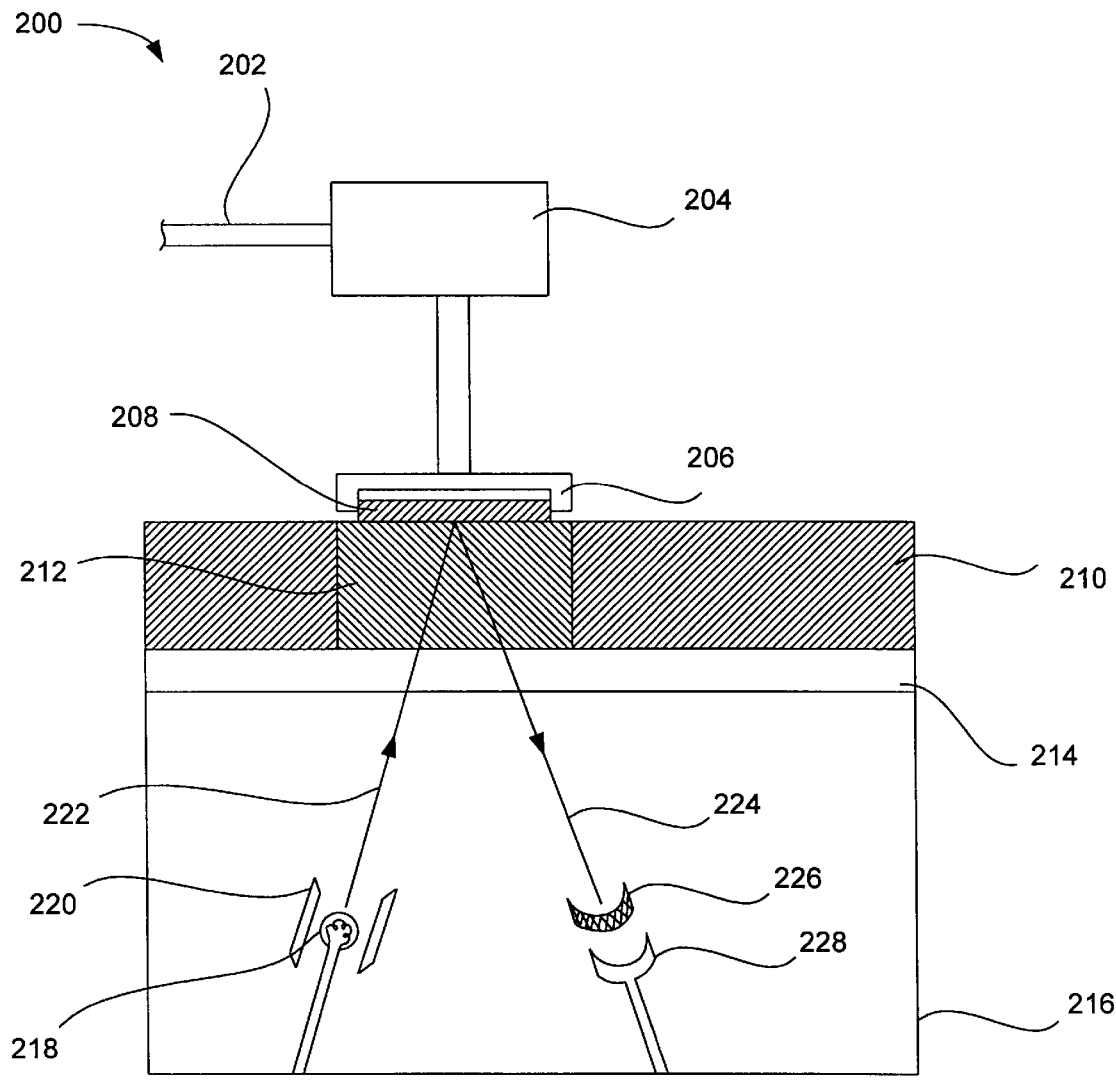
FIG. 2A is a cross-sectional view of an endpoint detection apparatus, which detects a reflected radiation signal, according to one embodiment of the present invention, from an integrated circuit (IC) substrate surface undergoing chemical-mechanical polishing.

FIG. 2A shows some significant components of an endpoint detection apparatus 200, according to one embodiment of the present invention, for detecting the presence of residual metal regions on an IC substrate surface that is undergoing CMP. Apparatus 200 includes a substrate holder arm 202 having disposed on one end a substrate holder motor 204 connected to a substrate holder 206, which secures an IC substrate 208. IC substrate 208 during CMP contacts a polishing pad 210, which is disposed above a platen 214 and includes a radiation transparent region 212. A radiation source 218 fitted with deflectors 220 and a reflected radiation signal detector 228 are positioned inside a housing 216, at least a part of which is disposed below platen 214. A band pass filter 226 is placed between radiation signal detector 228 and IC substrate 208 to filter out the ambient noise level in the reflected radiation signal during detection.

According to the present invention, before endpoint detection apparatus 200 begins detecting for residual metal, IC substrate 208 is secured on substrate holder 206 such that an active surface, including the die components, is facing down on polishing pad 210. Substrate holder motor 204 and a table motor (not shown to simplify illustration) for platen 214 are energized to rotate IC substrate 208 and rotate or put polishing pad 210 into an orbital state so that CMP may commence. During CMP, IC substrate 208 rotates against polishing pad 210, which is in turn rotating or in an orbital motion. Radiation source 218 may then be turned on and deflectors 220 ensure that as radiation transparent region 212 passes underneath IC substrate 208, a substantial amount of incident radiation 222 passes through platen 214, radiation transparent region 212 and illuminates at least a portion of the substrate surface. Almost instantly, i.e. within a few milliseconds, a resulting reflected radiation signal 224 reflected off the substrate surface passes through radiation transparent region 212, platen 214 and is filtered through band pass filter 226 before it is detected by radiation signal detector 228.

In the apparatus of FIG. 2A, radiation source 218 includes radiation generating devices such as infrared radiation lamps and halogen lamps. In a preferred embodiment, however, the radiation source of the present invention includes Sylvania type FEL lamp, which is commercially available from Osram Sylvania Inc. of Danvers, Mass. The Sylvania type FEL lamp generally operates at a power of about 1000 watts and generates wavelengths that range between about 1.5 to about 14 micrometers ($\mu$m). Radiation detector 228 may include detectors that are employed to detect infrared radiation. Radiation detectors may include detectors that are employed to detect infrared radiation. By way of example, radiation detectors may include FD1000W2.2 and FD1000W2.5 detectors, which are commercially available from Fermionics Corporation, of Simi Valley, Calif. Those skilled in the art will recognize that platen 214 may be made of radiation transparent materials such as silicon, etc., which allows radiation to pass therethrough, or have a gap filled or unfilled equal to or just greater than the area of an insert of the pad, so that radiation may be incident upon the overlying substrate 208.

Deflectors 210 and 220 may include materials well known in the art, such as well known standard reflectors with gold, silver, or aluminum. In one preferred embodiment, the deflectors employed in the present invention may include a Second Surface Silver Reflectors, which are commercially available from Optical Components, Inc., of Covina, Calif. because it eliminates almost all reflectivity losses during radiation deflection in the near-infrared region. Band pass filters 226 may include any of the custom filters commercially available from Optical Components Inc. mentioned above.

Figure 2B:
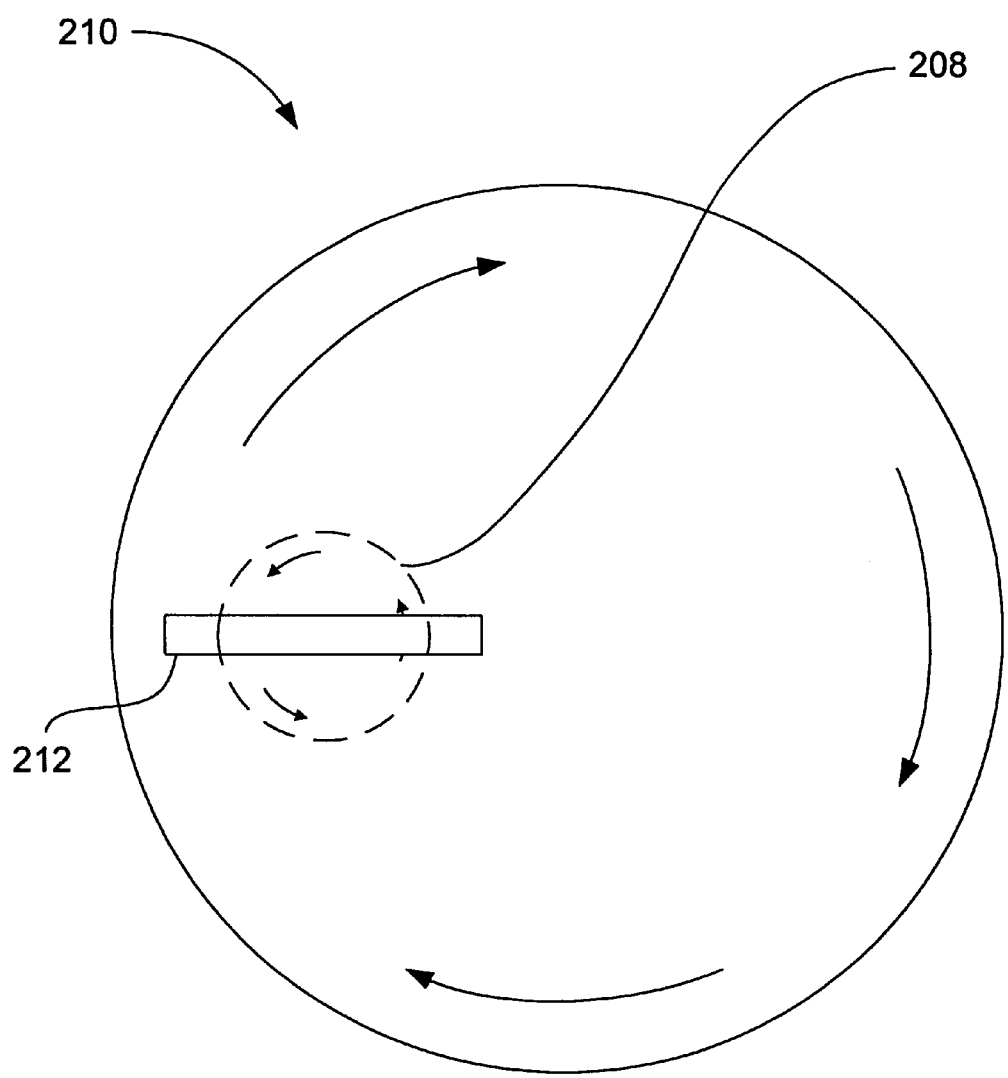
FIG. 2B shows a top view of a polishing pad, according to one embodiment of the present invention, including a radiation transparent region that is capable of scanning an entire integrated circuit (IC) substrate surface that is undergoing chemical-mechanical polishing.

FIG. 2B is a top view of a polishing pad, according to one embodiment of the present invention, that may be employed in the endpoint detection apparatus of FIG. 2A. Polishing pad 210 includes radiation transparent region 212, which allows an incident and reflected radiation beam to pass therethrough. During CMP, when IC substrate 208 is rotating and polishing pad 210 is rotating or in an orbital state, radiation transparent region 212 passes underneath the surface of IC substrate 208 and the incident radiation passing through radiation transparent region 212 is thereby exposed to the substrate surface. The resulting reflected radiation signal from the substrate surface passes through radiation transparent region 212 and is detected by radiation detector 228 over a period of time. In a preferred embodiment of the present invention, during this period of time, the reflected radiation signal for almost the entire substrate surface is detected through radiation transparent region 212. In this manner, radiation transparent region 212 may facilitate in effectively scanning almost the entire surface of IC substrate 208 with radiation.

Polishing pad 210 typically includes materials that may include at least one of urethane, polyurethanes, felt, polymer and a filler material. Polishing pad 210 may be large enough to polish a single substrate or multiple substrates simultaneously. By way of example, the polishing pad in the CMP apparatus IPEC 472, available from IPEC of Phoenix, Ariz., typically polishes a single wafer and the polishing pad employed in CMP apparatuses Speedfam V available from Speedfam of Chandler, Ariz., and Strausbaugh 6SP available from Strausbaugh of San Luis Obispo, Calif. polishes multiple wafers. Regardless of whether a single or multiple substrates are polished, the polishing pad may have a single radiation transparent region to detect for residual metal in a single or multiple substrates.

Radiation transparent region 212 may include any material that is transparent to radiation, preferably infrared radiation. Although it is possible to construct the entire polishing pad 210 from a radiation transparent material, it is preferable to have a window constructed from a radiation transparent material in a polishing pad that is substantially impermeable to radiation. The radiation transparent material may include at least one of silicon dioxide, magnesium oxide, polymetric material, urethane and polyurethane. By way of example, one method of manufacturing such a window in a polishing pad would be to cast a rod or plug of the radiation transparent material. A casting of the radiation transparent material is then inserted into the polymer of the polishing pad in its mold, while the polymer is still in liquid state to ensure that complete contact is made between the radiation transparent plug and the polishing pad polymer. After the polishing pad polymer has set it may be unmolded and sheets for polishing pads with a transparent window may be sliced from the casting.

The radiation transparent window made by the above-described method may be of any suitable dimension that provides incident radiation access to the entire substrate surface during CMP. By way of example, the dimensions of the window may approximate the size of the IC substrate or be in the form of a narrow slit, as shown in FIG. 2B. In the embodiment where the radiation transparent region 212 of the present invention is a narrow slit, the length of the slit may range any where from slightly larger than half the substrate surface diameter to slightly larger than the substrate surface diameter. In a preferred embodiment, however, the slit length is slightly larger than the substrate surface diameter and a slit width may be on the order of a few millimeters. For example, the slit length may be between about 3 and about 9 mm and the slit width may be between about 75 and about 450 mm. Those skilled in the art will recognize that for a better resolution of the reflected radiation signal from the substrate surface, a narrow slit is preferred.

Figure 3:
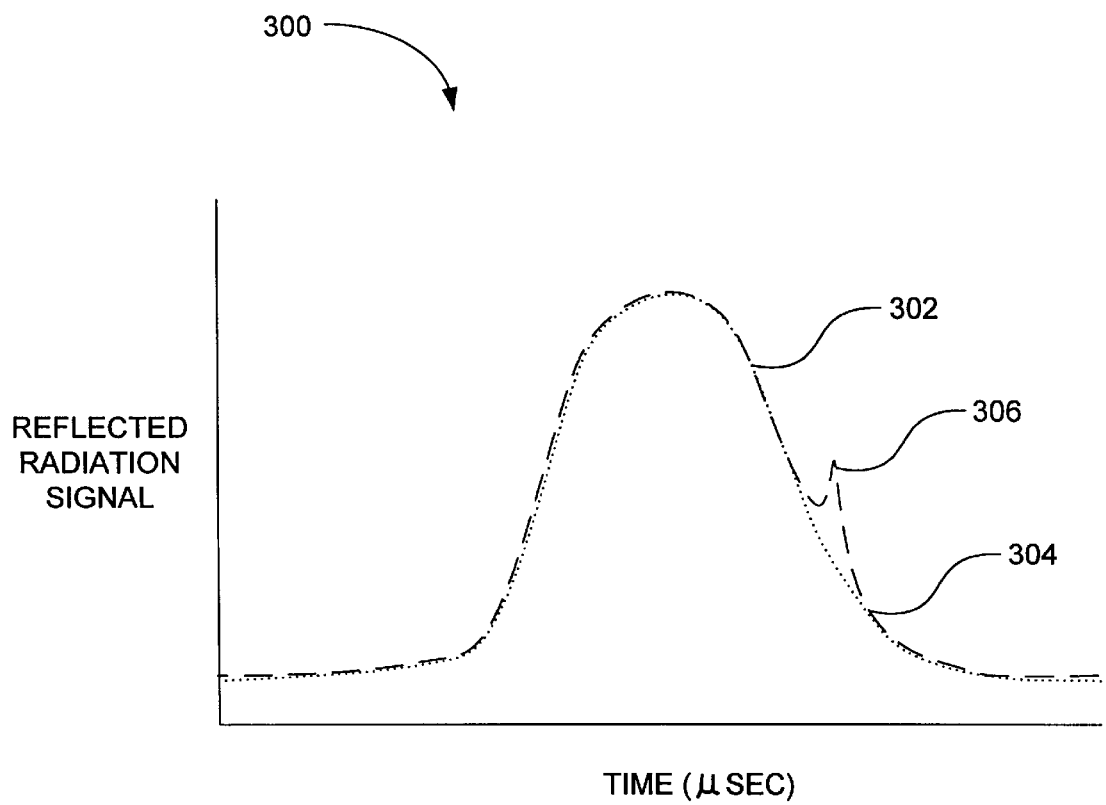
FIG. 3 is a graph of reflected radiation signal versus time for a production IC substrate superimposed over a baseline graph of reflected radiation signal versus time for a standard IC substrate that is substantially free of residual metal.

FIG. 3, for purposes of illustration, shows a graph or curve 302 of reflected radiation signal versus time for a production IC substrate (hereinafter referred to as "production substrate") undergoing CMP superimposed over a baseline graph or curve 304 in a graph of reflected radiation signal versus time obtained during CMP of a standard IC substrate (hereinafter referred to as "standard substrate"). As used in connection with the description of the invention, the term "production substrate" means IC substrates of a production lot that may ultimately be sold and the term "standard substrate" means an IC substrate that is substantially free of residual metal. In order to illustrate how residual metal can be detected according to the present invention, the production substrate employed to generate curve 302 includes residual metal. Thus, in FIG. 3, the graph of reflected radiation signal versus time of a production substrate surface including a residual metal region is compared with that of a standard substrate surface that is free of residual metal.

Referring to FIG. 3, initially, the reflected radiation signal in curves 302 and 304 mainly consists of a background noise signal (hereinafter referred to as "background noise"), which is substantially constant. The background noise is attributed primarily to the presence of metal interconnects, metallization layers, slurry particles, eroded metal particulates produced during CMP, the wafer holder, the substrate ceramic material, the substrate layers etc. The initial detection of a substantially constant background noise describes the scenario when no part of the radiation transparent region in the polishing pad is underneath the substrate surface. As the rotating or orbiting radiation transparent region approaches the rotating substrate and is positioned underneath an initial part of the substrate surface, however, the background noise of the reflected radiation signal begins to increase. The background noise increases almost linearly until a maximum reflected radiation signal is detected. The reflected radiation signal increases almost linearly because as the radiation transparent region proceeds to scan longer lengths of the substrate surface, it also scans larger substrate surface areas, which in turn provides larger background noise signals. The background noise signal, therefore, increases until the radiation transparent region is underneath the mid-point of the substrate surface, where the radiation transparent region scans the longest length, i.e. diameter, of the substrate surface. Thereafter, as the length of the substrate surface that is underneath the radiation transparent region reduces, the background noise signal also decreases accordingly.

A spike 306 in curve 302 indicates the presence of a residual metal region on the production substrate surface. The amplitude of spike 306 may depend on the amount of residual metal present on the substrate surface. By way of example, a greater amount of residual metal on the substrate surface will reflect the incident radiation to a greater extent, thereby producing a higher reflected radiation signal. The number of spikes in the above described graph of the production substrate may correspond to the number of residual metal regions present on the production substrate surface. By way of example, the substrate of FIG. 1 with four residual metal regions may have four distinct spikes, each corresponding to the presence of a residual metal region. Those skilled in the art will recognize that it may be possible to determine the proximate location of the residual metal region on the substrate surface based on the location of the spike on the curve.

While intending not to be bound by theory, the present invention recognizes that metals and silicon reflect radiation differently. Infrared radiation, for example, passes through a silicon layer, but reflects off a metal layer. Thus, before CMP or in the initial stages of CMP, when a small amount of the metal layer has been removed, a relatively thick layer of metal on the substrate surface will produce a relatively high reflected radiation signal. As the metal layer is depleted during CMP, the reflected radiation signal also decreases accordingly. The substrate surface, however, at this point may still have undesired regions, whose regions, whose presence is detected by the presence of spikes in the graph of reflected radiation signal versus time. When almost all of the metal layer, including the residual metal regions, is removed from the substrate surface, the reflected radiation signal off the substrate surface may be relatively weak, e.g., spike 306 of FIG. 3 subsides substantially. According to the present invention, when the area under the curve of reflected radiation signal versus time of a production substrate substantially matches or corresponds to that of a standard substrate that is free of residual metal, the CMP endpoint is attained. In other words, at the CMP endpoint the production substrate is substantially free of residual metal, just as the standard substrate.

Figure 4:
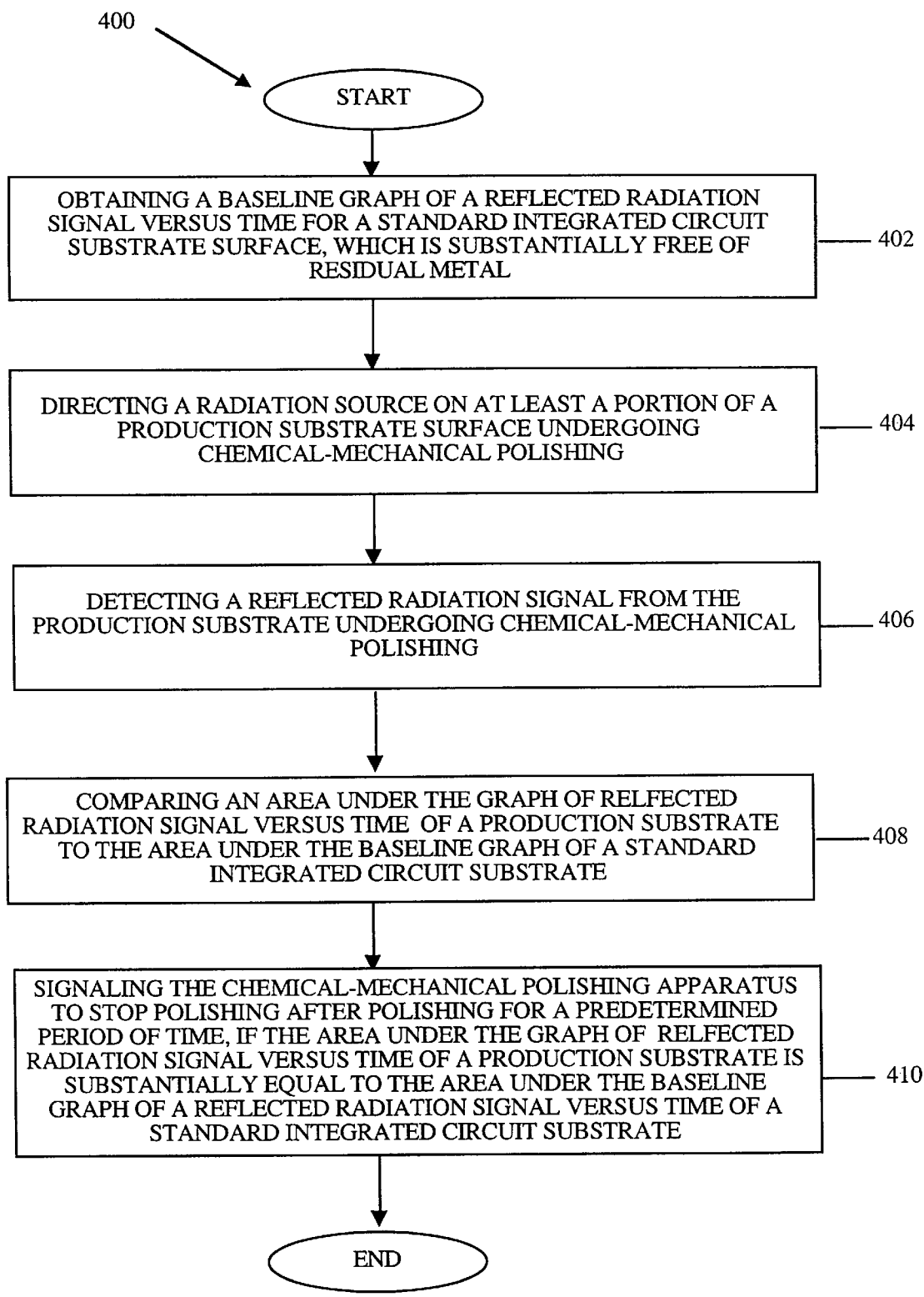
FIG. 4 is a flowchart of an endpoint detection process, according to one embodiment of the present invention, during chemical-mechanical polishing.

FIG. 4 shows an endpoint detection process 400, according to one embodiment of the present invention, that determines the CMP endpoint of a production substrate. Any endpoint detection apparatus that includes a radiation source, a detector and a polishing pad with a radiation transparent region may be employed to carry out endpoint detection process 400 according to the present invention. In preferred embodiments of the present invention, however, the apparatus 200 of FIG. 2A may be implemented to carry out process 400.

Endpoint detection process 400 of the present invention begins with a step 402, which includes obtaining a baseline graph or curve of reflected radiation signal versus time for a standard substrate. The standard substrate is substantially free of residual metal and serves to provide a baseline or a reference curve of reflected radiation signal versus time, against which the curve of reflected radiation signal versus time of production substrates may be compared.

The baseline curve of reflected radiation signal versus time can be obtained by employing the apparatus of FIG. 2A, for example. After the standard surface is secured on wafer holder 206 and CMP conditions of a production substrate are simulated, radiation source 218 is then energized to illuminate the standard substrate surface and a resulting reflected radiation signal is then detected over a period of time. A curve, similar to curve 302 of FIG. 3, may be generated and stored as a baseline graph or curve of reflected radiation signal versus time of a standard substrate. In one embodiment of the present invention, step 402 may be carried out and stored before production substrates undergo CMP.

In order to obtain a precise baseline curve of the standard substrate that appropriately accounts for the background noise signal produced during the reflected radiation signal detection of the production substrate, the standard substrate employed in step 402 preferably includes the various layers, e.g., dielectric and metallization layers, between the residual metal regions and a silicon substrate layer of the production substrate. In the baseline curve of reflected radiation signal versus time, some of the radiation incident upon the standard substrate surface passes through the substrate surface or is reflected off the substrate surface at a much lower rate because the standard substrate layer includes silicon that is free of residual metal. The baseline reflected radiation signal of the standard substrate primarily accounts for the presence of metal interconnects and metallization layers, which may similarly be present in the production substrate. However, radiation reflected off of the wafer holder, substrate ceramic material, substrate layers etc., may also contribute significantly to the detected baseline reflected radiation signal, which constitutes as the background noise during CMP.

Next, a step 404 includes directing a radiation source on at least a portion of a production substrate surface. By way of example, this may be accomplished by using radiation source 218 described in the apparatus shown in FIGS. 2A. A step 406 then includes detecting and measuring the resulting reflected radiation signal from the production substrate surface over time. Steps 404 and 406 are relatively fast, i.e. a period of time required to complete steps 404 and 406 is on the order of a few milliseconds. By the end of step 406, a graph of reflected radiation signal versus time for a production substrate may be generated. An example of such a graph is curve 304 shown in FIG. 3. In the case of the polishing pad that polishes multiple substrates simultaneously, the graphs of reflected radiation signal versus time generated for the various substrates may be coordinated with the rotating or orbital motion of the platen to keep track of which graph is associated with a particular substrate undergoing CMP. Those skilled in the art will recognize that such coordination may be carried out by a computer system.

It should be borne in mind that every time the radiation transparent region in the polishing pad scans the production substrate surface during CMP, a graph or curve of reflected radiation signal versus time is generated. As the metal layer is removed from the production substrate undergoing CMP, the curve of reflected radiation signal versus time begins to look more and more like the curve of standard substrate generated in step 402. If, however, the production substrate surface still has some residual metal regions near the end of CMP, the curve of reflected radiation signal versus time of production substrate includes spikes, an example of which is shown as spike 306 in curve 304 of FIG. 3.

Next, in a step 408, an area under the curve of reflected radiation signal versus time of the production substrate obtained in step 406 is compared to an area under the baseline curve of the standard substrate stored in step 402. Those skilled in the art will recognize that such areas are computed by integrating the detected reflected radiation signal over time, which ranges from the time when the first signal was detected to the time when the last signal was detected for a particular scan. By way of example, FIG. 3 shows such a comparison between graphs of production and standard substrates. In FIG. 3, the area under curve 304 (of the production substrate) is larger than the area under curve 302 (of the standard substrate) because curve 304 has spike 306, which indicates the presence of a residual metal region. Of course CMP of the production substrate proceeds normally, if residual metal regions are detected as described above. It is also important to note that when all or almost all of the residual metal is removed from the production substrate surface, the area under the curve of reflected radiation signal versus time of the production substrate surface approaches a constant value.

Finally, a step 410 includes signaling the CMP apparatus to stop polishing after polishing for a predetermined period of time, if the area under the curve of reflected radiation signal versus time of a production substrate is substantially equal to the baseline curve of the standard substrate. By way of example, when the area under graphs 304 and 302 are substantially equal, i.e. all or most of the residual metal region present on the production substrate (used to generate graph 304 in FIG. 3) has been removed during CMP, and the spike has substantially subsided, then the CMP apparatus, e.g., apparatus 200 shown in FIG. 2A, is signaled to stop polishing after polishing for a predetermined time. Therefore, when the areas under the curves of reflected radiation signal versus time for production and standard substrates are substantially equal, according to the present invention the CMP endpoint is attained. After CMP endpoint has been attained, polishing may still continue for a predetermined time. The predetermined time may be any amount of time that ensures that the wafer layer being polished is removed completely and the other production substrate surface layers are not damaged. The predetermined time in a preferred embodiment of the present invention may vary from between about 2 and about 5 seconds.

In one embodiment of the present invention, depending on the information obtained, e.g., presence and/or amplitude of spikes, etc., after comparing the areas under the graphs of the production and standard substrate in step 408, immediate feedback may be provided to the CMP apparatus. The feedback may include modification of polishing parameter values, e.g., polishing time of the production substrate and pressure applied by the production substrate against the polishing pad, etc. Thus, any corrections that need to be made to the CMP settings may be made almost instantly.

Suitable computer systems for use in implementing and controlling the automated methods in the present invention, e.g., energizing radiation sources or activating detectors, storing baseline graphs of reflected radiation signal versus time, comparing the area under the baseline graph to the graphs of reflected radiation signal versus time of production substrates, coordinating the graphs of reflected radiation signal versus time to the rotating or orbital motion of the platen, etc., may be obtained from various vendors. In one preferred embodiment, an appropriately programmed HP735 workstation (Hewlett Packard, Palo Alto, Calif.) or Sun ULTRASPARC or Sun SPARC (Sun Microsystems, Sunnyvale, Calif.) may be employed in an IBM PC based system or a VM bus controller.

It should be understood that the present invention also relates to machine readable media on which are stored instructions for implementing the invention. Such instructions facilitate the comparison of the area under the baseline graph of the standard substrate and the area under the graph of production substrate and the provision of feedback to the CMP process regarding the various polishing parameter settings based on a certain predetermined criteria. Such media includes, by way of example, magnetic disks, magnetic tape, optically readable media such as CD ROMs, semiconductor memory such as PCMCIA cards, etc. In each case, the medium may take the form of a portable item such as a small disk, diskette, cassette, etc., or it may take the form of a relatively larger or immobile item such as a hard disk drive or RAM provided in a computer.

Figure 1:
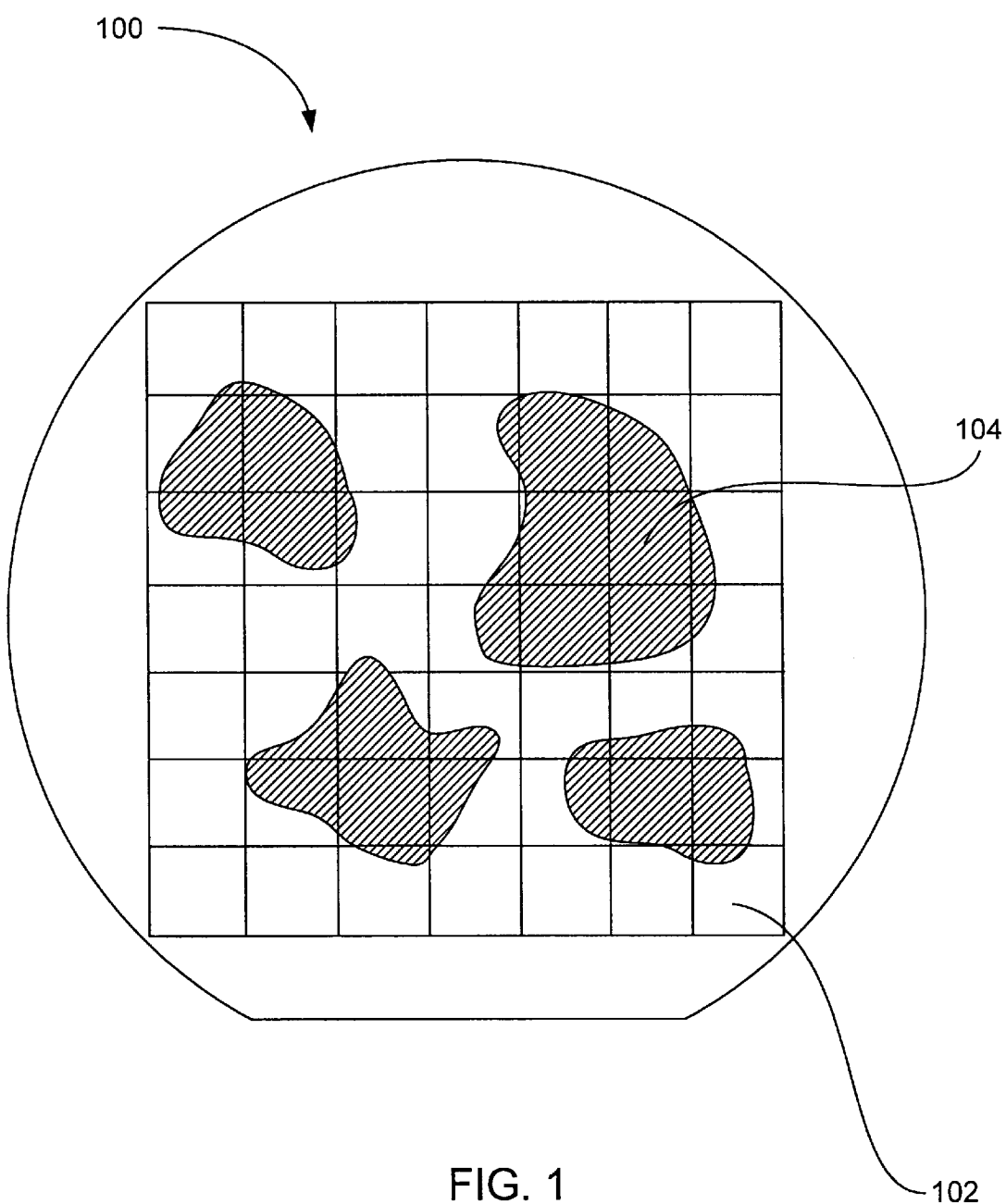
FIG. 1 is a top view of a semiconductor wafer surface having residual metal regions, which are formed when a motor current measuring mechanism determines the endpoint of a chemical-mechanical polishing process.

The endpoint detection processes of the present invention represents a marked improvement over the current endpoint detection processes. By way of example, the endpoint detection system of the present invention provides a more precise endpoint during CMP because it may be configured to scan the entire substrate surface and thereby eliminate substantially all the residual metal regions. Thus, the presence of residual metal regions on the substrate surface, as shown in FIG. 1 and encountered when detecting the endpoint by the conventional motor current method are substantially eliminated. This translates into a higher yield for the die. As a further example, the present invention essentially requires a radiation source, a detector, and a polishing pad with a radiation transparent region, all of which are relatively inexpensive and easy to implement. Such equipment can be easily integrated into the CMP apparatus, e.g. CMP apparatus 200 as shown in FIG. 2A, with minor modifications. Further still, the endpoint detection system may also provide immediate feedback to the CMP apparatus under operation to correct CMP parameters for effective polishing.

Although the foregoing invention has been described in some detail for purposes of clarity of understanding, it will be apparent that certain changes and modifications may be practiced within the scope of the appended claims. For example, while the specification has described in terms CMP, there is in principle no reason why features of this invention cannot be adapted or implemented for detecting the amount of metal on an integrated circuit substrate surface in other applications. Therefore, the present embodiments are to be considered as illustrative and not restrictive, and the invention is not to be limited to the details given herein, but may be modified within the scope of the appended claims.

What is claimed is:

1. An automated endpoint detection process for detecting residual metal on a surface of an integrated circuit substrate during chemical-mechanical polishing, comprising:

obtaining a baseline graph of reflected radiation signal versus time of radiation exposure for a surface on a standard integrated circuit substrate that is substantially free of residual metal;

directing radiation generated from a radiation source through a radiation transparent region of a polishing pad such that radiation is incident on at least a portion of a surface of the integrated circuit substrate;

detecting a reflected radiation signal from said surface of said integrated circuit substrate through the radiation transparent region of the polishing pad;

comparing an area under a graph of said reflected radiation signal versus time of radiation exposure obtained for said surface of said integrated circuit to said baseline graph of said surface of said standard integrated circuit substrate and thereby determining whether residual metal is present on said surface of said integrated circuit substrate; and signaling a chemical-mechanical polishing assembly to stop polishing after polishing for a predetermined time, if said area under said graph of said reflected radiation signal versus time of radiation exposure obtained for said surface of said integrated circuit is substantially equal to said baseline graph of said surface of said standard integrated circuit substrate.

2. The process of claim 1, wherein the step of comparing the area under the graph of the reflected radiation signal versus time of radiation exposure obtained for the integrated circuit to the baseline graph of the standard integrated circuit substrate is facilitated by a computer system.

3. The process of claim 1, wherein the step of obtaining the baseline graph of the reflected radiation signal versus time of radiation exposure for the surface on the standard integrated circuit substrate is conducted before the step of polishing.

4. The process of claim 1, wherein the radiation source comprises an infrared radiation source and the step of detecting comprises using a radiation detector that includes an infrared radiation detector.

5. The process of claim 1, wherein the integrated circuit substrate comprises a semiconductor wafer.

6. The process of claim 1, wherein during the step of directing substantially all of the surface of the integrated circuit is exposed to radiation through the radiation transparent region in the polishing pad, which is rotating or in an orbital state.

7. The process of claim 1, wherein the step of obtaining the baseline graph of reflected radiation signal versus time of radiation exposure comprises:

providing radiation to the surface of the standard integrated circuit substrate that is substantially free of residual metal through the radiation transparent region of the polishing pad, which is rotating or in an orbital state, such that radiation is incident on at least a portion of the surface of the standard integrated circuit substrate;

detecting the baseline reflected radiation signal from the surface of the standard integrated circuit substrate through the radiation transparent region of the polishing pad over a period of time, during which substantially all of the surface of the standard integrated circuit substrate is scanned by radiation; and storing the baseline graph of reflected radiation signal versus time of radiation exposure from the surface of the integrated circuit substrate on machine readable media.

8. The process of claim 1, wherein the polishing pad comprises at least one material selected from the group consisting of urethane, polyurethane, felt, polymer and a filler material.

9. The process of claim 1, wherein the radiation transparent region comprises at least one material selected from the group consisting of silicon dioxide, magnesium oxide, polymetric material, urethane and polyurethane.

10. The process of claim 1, wherein the step of signaling is carried out by a computer system.

11. The process of claim 1, wherein the predetermined time comprises between about 2 and about 5 seconds.

12. The method of claim 1 wherein said reflected radiation is obtained over a period of time during which essentially the entire substrate surface is scanned by radiation passing through the radiation transparent region of the polishing pad.

* * * * *